United States Patent [19]

Grakauskas

[11] 4,233,250

[45] Nov. 11, 1980

[54] PROCESS FOR SYNTHESIZING THE ALKALI METAL SALTS OF DINETROMETHANE

[75] Inventor: Vytautos Grakauskas, Arcadia, Calif.

[73] Assignee: The United States of America as represented by the Secretary of the Air Force, Washington, D.C.

[21] Appl. No.: 33,610

[22] Filed: Apr. 26, 1979

[51] Int. Cl.³ .............................................. C07C 76/02
[52] U.S. Cl. ................................ 568/926; 260/465.1; 560/156; 568/842; 568/852
[58] Field of Search ........................... 260/465.1, 644; 560/156

[56] References Cited

U.S. PATENT DOCUMENTS

| | | | |
|---|---|---|---|
| 2,161,475 | 6/1939 | Landon | 260/644 |
| 2,597,027 | 5/1952 | Passino et al. | 260/644 |
| 3,067,261 | 12/1962 | Clark et al. | 260/644 |
| 3,378,596 | 4/1968 | Toops, Jr. et al. | 260/644 |
| 3,387,044 | 6/1968 | Grakauskas et al. | 260/644 |
| 3,706,808 | 12/1972 | Bachman et al. | 260/644 |

*Primary Examiner*—Leland A. Sebastian
*Attorney, Agent, or Firm*—Joseph E. Rusz; William J. O'Brien

[57] ABSTRACT

A process for synthesizing the alkali metal salts of dinitromethane by effecting the saponification of methyl cyanodinitroacetate previously prepared by the nitration of methyl cyanooximinoacetate.

4 Claims, No Drawings

PROCESS FOR SYNTHESIZING THE ALKALI METAL SALTS OF DINETROMETHANE

STATEMENT OF GOVERNMENT INTEREST

The invention described herein may be manufactured and used by or for the Government for governmental purposes without the payment of any royalty thereon.

BACKGROUND OF THE INVENTION

This invention relates to dinitromethane and to a process for synthesizing its alkali metal salts. More particularly, this invention concerns itself with an economical and practical route for synthesizing the alkali salts of dinitromethane which involves the use of methyl cyanooximinoacetate and methyl cyanodinitroacetate as reaction components.

The salts of dinitromethane find wide use as intermediate and starting materials in the preparation of polynitro explosives and advanced energetic propellants. They also find application as reaction components in the preparation of a wide variety of geminal dintrocompounds. The variety of applications for which these materials find use amply demonstrates their importance to the chemical industry. Unfortunately, the methods utilized in the past for effecting the synthesis of the alkali metal salts of this invention, did not provide an efficient and economical means for their production in reasonably large quantities. The necessity for providing a practical route which could lead to reduced cost production, therefore, become obvious.

Free dinitromethane is an unstable pale yellow oil that decomposes vigorously even at ambient temperatures. The alkali salts of dinitromethane, however, are stable compounds having a wide utility as key intermediates in chemical syntheses.

The potassium salt of dinitromethane was first prepared by the reduction of potassium bromonitromethane with hydrogen sulfide in accordance with the method of F. Villiers, Bull. Soc. Dhim. Fr., 41, 251 (1884). More recently, potassium dinitromethane has been prepared by the Ter Meer reaction of chloronitromethane as shown in H. Ferer et al, J. An. Chem. Soc., 73 1360 (1951). Unfortunately, this reaction only produces yields of about 23 percent. The dinitromethane salts can also be obtained from the alkali salts of dinitroethanal according to the methods shown by P. Noble et al, Chem, Rev., 64 19 (1964).

The alkali salts of dinitromethane have proven to be very useful as starting materials in the synthesis of geminal dinitro compounds. For example, potassium dinitromethane reacts readily with one or two mole of formaldehyde to give potassium dinitroethanal and 2,2-dinitropropanedial, respectively. The fluorination of alkali salts of dinitroethanol, in turn, produces fluordinitroethanol. Fluorodinitromethane and 4,4-dinitropimelic acid are other geminal dinitro intermediates found to be useful in the synthesis of polynitro explosives and propellants.

From the above examples, it can be seen that dinitromethane salts are important and find wide application as key intermediates in a variety of chemical syntheses. Consequently, a considerable research effort has evolved in an attempt to find efficient economical and practical routes for preparing the alkali salts of dinitromethane.

Heretofore, the lack of a practical route necessitated the use of methods based on the Ter Meer method, the use of nitroform, or the oxidative nitration reaction.

Nitroform, used in the synthesis of fluorodinitroethanol, is produced by nitration of acetylene or acetone. Both processes produce large amounts of nitrogen oxides which present expensive pollution problems. In its applications, for the synthesis of gemminal dinitro compounds, one nitro group of nitroform must be removed adding to the cost of this process.

In the oxidative nitration route, gem-dinitro compounds are prepared by reacting mononitro compounds with a mixture of silver nitrate and sodium nitrite. In a large scale production this method requires a large capital investment in silver nitrate and also suffers from mechanical losses of silver.

The Ter Meer reaction is limited to the synthesis of terminal geminal dinitro compounds. As already indicated, the yield of dinitromethane in the Ter Meer method is low. Also, in many cases, nitrohalo starting materials needed in this reaction cannot be obtained in good yields. With the present invention, however, the problems associated with these prior art methods have been overcome by the process of this invention in which the synthesis of the alkali metal salts of dinitromethane has been accomplished by effecting the nitration of methyl cyanooximinoacetate to form methyl cyanodinitroacetate which in turn is reacted with an alkali metal hydroxide, such as potassium or sodium hydroxide, to effect its saponification and resulting production of the respective alkali metal salt of dinitromethane. This unique method provides a solution to the problem of finding a practical and economical route for synthesizing these useful intermediate reactants, in relatively high yield.

SUMMARY OF THE INVENTION

In accordance with this invention a practical and economical route has been found for synthesizing the alkali metal salts of dinitromethane in relatively high yield. The synthesis is accomplished by effecting the nitration of methyl cyanooximinoacetate followed by the step of saponifying the resulting methyl cyanodinitroacetate to produce the desired alkali metal salts.

Accordingly, the primary object of this invention is to provide a practical route for the synthesis of the alkali metal salts of dinitromethane.

Another object of this invention is to provide a method for synthesizing the alkali metal salts of dinitromethane in relatively high yield that is both economical and readily adaptable to large scale industrial use.

Still another object of this invention is to provide a method for synthesizing the alkali metal salts of dinitromethane that involves the nitration of methyl cyanooximinoacetate followed by the saponification of the resulting nitrated reaction product.

The above and still other objects and advantages of the present invention will become more readily apparent upon consideration of the following detailed disclosure thereof.

DETAILED DESCRIPTION OF THE PREFERRED EMBODIMENT

In accordance with this invention it has been found that a practical route to the synthesis of the alkali metal salts of dinitromethane can be accomplished by a process based on cyandinitromethide salts.

From C. O. Parker, Tetrahedron, 17, 109 (1962), it is known that the nitration of methyl cyanoacetate with the mixed acid gives relatively low yields of about 20 to 30 percent of the dinitro derivation. He also reported much better yields of methyl cyanodinitroacetate (80–85%) in the nitration of methyl cyanoximinoacetate, available quantitatively in the nitrosation of cyanoacetate with sodium nitrite-phosphoric acid in accordance with the following reaction:

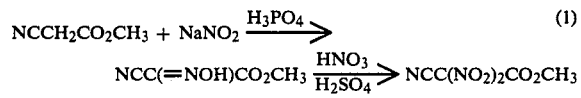
(1)

Methyl cyanodinitroacetate in methylene chloride solution reacted with water at ambient temperatures to give the known dinitroacetronitrile according to the reaction:

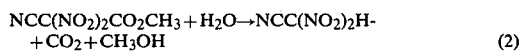
(2)

When an aqueous solution of dinitroacetonitrile salt was heated with 2 mol of an alkali hydroxide, the nitrile under went saponification to give the respective alkali metal salt of dinitromethane, the alkali carbonate, and ammonia according to the reaction:

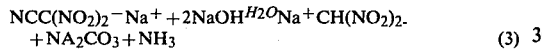
(3)

The rate of reaction (3) above was conveniently followed by the disappearance of the nitrile UV absorption at 350 nm. The reaction was completed in ca. 2 h at 80°–85° C., and the yield of dinitromethane salt was practically quantitative. At 105° C. the saponification was completed in 15–20 min.

Sodium dinitromethane solution, obtained in this one-pot reaction can be used directly in the synthesis of other geminal dinitro compounds. For example, formaldenyde (1 mol) was added, and the resulting sodium dinitroethanol was fluorinated according to known procedures to give fluorodinitroethanol in 70–80% yields. Equation 4, as follows, illustrates his reaction:

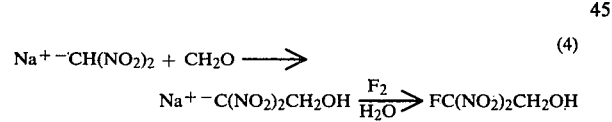
(4)

Similarly, sodium dinitromethane solution can be used directly in the synthesis of 2,2 dinitropropanediol. Formaldehyde (2 mol) is added, and the alkaline solution then neutralized with acetic acid to give the diol according to the following reaction:

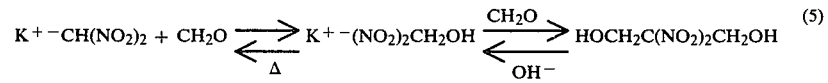
(5)

The process of the invention is further illustrated in a more specific manner by the following examples which show the preparation of potassium dinitromethane in accordance with this invention.

EXAMPLE 1

A stirred suspension of 3.4 g (0.02 mol) of potassium cyanodinitromethide in 15 ml of 10% aqueous potassium hydroxide was heated at 90°–95° C. for 2 h. Ammonia odor, strong at the beginning, gradually faded away. The yellow solution was cooled to 0°–5° C. The yellow crystalline solid was collected and washed with two 5 ml portions of ice-water 2.5 g (85% yield): mp 220° C. (expl).

EXAMPLE 2

To a suspension of 1.5 g of 85% potassium hydroxide (0.023 mol of KOH) in 15 ml of water was added 3.4 g (0.02 mol) of potassium cyanodinitromethide and the mixture was heated at 90°–95° C. for 2.5 hours. The solution was cooled to 0°–5° and potassium dinitromethane was collected by filtration and washed with three 4 ml portions of ice-water. The air-dried material weighed 2.5 g (85% yield), mp 220° (expl).

From a consideration of the above, it can be seen that the present invention provides a simple, practical and economic process for producing the alkali salts of dinitromethane in very high yield. Obviously, various modifications of the invention can be made in view of the present disclosure. However, it is to be understood that all such modifications as are encompassed within the purview of the appended claims are intended to be included herein.

What is claimed is:

1. A process for preparing the alkali metal salts of dinitromethane which comprises the steps of
    (A) effecting the nitration of methyl cyanooximinoacetate to produce methyl cyanodinitroacetate;
    (B) effecting the hydrolysis of the resulting cyanodinitroacetate to produce dinitroacetonitrile;
    (C) effecting the neutralization of said dinitroacetonitrile with an alkali metal hydroxide to produce the corresponding alkali metal salt of cyanodinitromethide; and
    (D) effecting the saponification of said cyanodinitromethide salt with an aqueous solution of an alkali metal hydroxide at a temperature and for a time period sufficient to produce the corresponding alkali metal salt of dinitromethane.

2. A process in accordance with claim 1 wherein said methyl cyanooximinoacetate is produced by the nitrosation of methyl cyanoacetate with sodium nitrile-phosphoric acid.

3. A process in accordance with claim 1 wherein said saponification takes places within a temperature environment of from about 90° to 95° C. for a period of about 2.0 to 2.5 hours.

4. A process in accordance with claim 3 wherein said aqueous alkali metal hydroxide is selected from the group consisting of sodium hydroxide and potassium hydroxide.

* * * * *